US009926243B2

United States Patent
Wang et al.

(10) Patent No.: US 9,926,243 B2
(45) Date of Patent: *Mar. 27, 2018

(54) PROCESS AND DEVICE FOR SEPARATION BY SIMULATED MOVING BED ADSORPTION

(75) Inventors: Dehua Wang, Beijing (CN); Zhuo Yu, Beijing (CN); Huiguo Wang, Beijing (CN); Jianfeng Ma, Beijing (CN)

(73) Assignees: China Petroleum & Chemical Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 617 days.

This patent is subject to a terminal disclaimer.

(21) Appl. No.: 14/234,807

(22) PCT Filed: Jul. 16, 2012

(86) PCT No.: PCT/CN2012/000956
§ 371 (c)(1),
(2), (4) Date: Jan. 24, 2014

(87) PCT Pub. No.: WO2013/013493
PCT Pub. Date: Jan. 31, 2013

(65) Prior Publication Data
US 2014/0155674 A1 Jun. 5, 2014

(30) Foreign Application Priority Data
Jul. 28, 2011 (CN) .......................... 2011 1 0213323

(51) Int. Cl.
*B01D 15/02* (2006.01)
*B01D 15/18* (2006.01)
(Continued)

(52) U.S. Cl.
CPC ................. *C07C 7/12* (2013.01); *B01D 15/02* (2013.01); *B01D 15/1835* (2013.01); *C07C 7/13* (2013.01)

(58) Field of Classification Search
CPC .. C07C 7/12; C07C 7/13; B01D 15/02; B01D 15/1835
See application file for complete search history.

(56) References Cited

U.S. PATENT DOCUMENTS 2,985,589 A    5/1961   Broughton et al.
3,040,777 A    6/1962   Carson et al.
(Continued)

FOREIGN PATENT DOCUMENTS

CN    1106370 A    8/1995
CN    1379007 A    11/2002
(Continued)

OTHER PUBLICATIONS

Ruthven, D.B., et. al., *Counter-Current and Simulated Counter-Current Adsorption Separation Processes*, Chemical Engineering Science, 44(5):1011-1038 (1989).
(Continued)

*Primary Examiner* — Lucas A Stelling
(74) *Attorney, Agent, or Firm* — Finnegan, Henderson, Farabow, Garrett & Dunner, LLP (57) ABSTRACT

The present invention relates to a process for separating isomers by simulated moving bed (SMB) adsorption, comprising separating the raw materials comprising isomers by SMB adsorption, said SMB comprising many adsorption beds each of which is equipped with grids, each of the grids being equipped with the feedstock inlet and outlet pipeline of the bed, the feedstock charged into and discharged from SMB at least comprising feedstocks, desorbent, extract, and raffinate, the extract being enriched with the target product,
(Continued)

characterized in that the extract is used as a flushing liquid and respectively charged to first or second bed at the upstream of the feedstock charging position and to one of second to fourth beds at the downstream of the extract withdrawing position. Such process is used for separation of $C_8$ aromatic isomers by adsorption, and can improve the capacity of the device while effectively increasing the purity of the target product separated by adsorption.

7 Claims, 3 Drawing Sheets

(51) Int. Cl.
*C07C 7/12* (2006.01)
*C07C 7/13* (2006.01)

(56) References Cited

U.S. PATENT DOCUMENTS

| | | | |
|---|---|---|---|
| 3,201,491 A | 8/1965 | Stine et al. | |
| 3,626,020 A | 12/1971 | Neuzil | |
| 3,686,342 A | 8/1972 | Neuzil | |
| 3,997,620 A | 12/1976 | Neuzil | |
| 4,313,015 A | 1/1982 | Broughton | |
| 4,326,092 A | 4/1982 | Neuzil | |
| 5,750,820 A | 5/1998 | Wei | |
| 5,882,523 A | 3/1999 | Hotier et al. | |
| 5,884,777 A | 3/1999 | Pan et al. | |
| 5,972,224 A | 10/1999 | Hotier et al. | |
| 6,004,518 A | 12/1999 | Green | |
| 6,017,448 A | 1/2000 | Hotier et al. | |
| 6,149,874 A | 11/2000 | Hotier | |
| 6,222,088 B1 * | 4/2001 | Kulprathipanja | C07C 2/76 208/310 Z |
| 2002/0143223 A1 | 10/2002 | Leflaive et al. | |
| 2008/0269535 A1 | 10/2008 | Hotier et al. | |
| 2010/0305381 A1 * | 12/2010 | Go | B01D 15/1835 585/826 |

FOREIGN PATENT DOCUMENTS

| | | |
|---|---|---|
| CN | 101128490 | 2/2008 |
| CN | 101293807 A | 10/2008 |
| EP | 0722356 A1 | 3/1995 |
| FR | 2750886 A1 | 7/1996 |
| FR | 2751888 A1 | 7/1996 |
| JP | 09-502652 | 3/1997 |
| JP | 10-174801 | 6/1998 |
| JP | 10-512484 | 12/1998 |
| JP | 2011-506091 | 3/2011 |
| JP | 2012-528158 | 11/2012 |
| OA | 550 A | 7/1966 |
| WO | WO 1995/07740 A1 | 3/1995 |
| WO | WO 2010/1382484 A2 | 12/2010 |

OTHER PUBLICATIONS

Adsorbent Grid Feasibility Research, Thesis of Master Degree of University of Petroleum, Apr. 1, 2010.

* cited by examiner

PROCESS AND DEVICE FOR SEPARATION BY SIMULATED MOVING BED ADSORPTION

TECHNICAL FIELD

The present application relates to a process and device for separation of isomers by adsorption, specifically for separation and purification of hydrocarbons by simulated moving bed (SMB) adsorption.

BACKGROUND OF THE INVENTION

The adsorption separation is very effective for the separation of isomers having an extremely small boiling point difference, or of different components having different structural features, e.g. for the separation of p-xylene from other $C_8$ aromatic isomers, and of n-alkanes from hydrocarbons having other structures.

The separation process by SMB adsorption achieves countercurrent contact of the liquid and solid phases and increases the separation efficiency. U.S. Pat. No. 2,985,589, U.S. Pat. No. 3,201,491, U.S. Pat. No. 3,626,020, U.S. Pat. No. 3,686,342, U.S. Pat. No. 3,997,620 and U.S. Pat. No. 4,326,092 describe the separation device and process by SMB adsorption, and use thereof for separation of p-xylene and m-xylene. Douglas M. Ruthven summarizes in *Chemical Engineering Science* (1989, v44(5):1011-1038) the principle, development, test and model study and industrial process of the separation process by continuous countercurrent adsorption.

Typical SMB adsorption separation comprises at least two streams of feedstocks, i.e. feedstock (F) and desorbent (D), and at least two streams of the discharged materials, i.e. extract (B) and raffinate (R), wherein the extract is enriched with the target product. The positions at which each stream of the feedstocks is fed into or discharged from the adsorption column are moved periodically, and the feedstocks along with the flow direction of the feedstocks in the adsorption column are in a sequence of the desorbent (D), extract (E), feedstock (F) and raffinate (R). The circulation of feedstocks in the adsorption column makes up an closed-loop. The device for controlling the charging and discharging of the feedstocks to and from the adsorption column may be a rotary valve, or a series of on-off valves.

During the adsorption separation, many streams of feedstocks share the delivery pipelines to be charged into or discharged from the adsorption column. The pipeline discharged into and discharged from a certain bed position of the adsorption column will pass the raffinate (R), feedstock (F), extract (E) and desorbent (D) in turn. The previous residual materials in the pipeline will pollute the materials passing through the pipeline, thereby rendering adverse effect on the separation by SMB adsorption. In particular, when the separation by SMB adsorption is used to product high purity products, the residual feedstocks in the pipelines will pollute the extract.

U.S. Pat. No. 3,201,491 discloses a process for increasing the purity of the product continuously separated by adsorption. As for the circumstance that the residual raw material pollutes the extract, it discloses "charging a flush stream comprising a fluid separable from said feed stock into the fluid inlet next upstream relative to the feed stream inlet in an amount not substantially exceeding the volume of fluid in the line of flow between the feed inlet into the fluid distribution center and the feed inlet to the contact zone receiving said feed stream" The flushing liquid is a desorbent-rich stream removed from a fixed mass of sorbent downstream from the desorbent inlet, or a sorbate-rich stream withdrawn from the farthermost downstream mass of sorbent comprising the desorption zone U.S. Pat. No. 5,750,820 discloses a multiple grade flush adsorption separation process, which is a process for separating the target product from a multicomponent feedstream, comprising introducing said feedstream through at least one fluid communication conduit into said apparatus; flushing said apparatus having at least one fluid communication conduit with a sufficient quantity of at least one initial flushing medium drawn from a first source and comprising said at least one desired component in an initial concentration, such that feedstream residue is flushed from said apparatus by said at least one initial medium; flushing said at least one fluid communication conduit with a sufficient quantity of a final flushing medium drawn from a second source and comprising said at least one desired component in a final concentration, such that said final concentration is greater than said initial concentration and such that initial medium residue from said conduit is flushed into said conduit into said apparatus by said final medium; and withdrawing said product from said apparatus, wherein said first source is separate from said second source and at least one of said first source and said second source is separated from said apparatus U.S. Pat. No. 5,972,224 discloses a process and device for improving the purity of a product in a simulated fluid bed, said device comprising a number of beds (A1 to An) of a solid or adsorbent that are contained in at least one adsorption column, a fluid distributor plate (Pi) between each bed, whereby each distributor plate is divided into a number of sectors (P10, P11, P12), whereby each distributor plate sector (Pi) includes at least one distribution chamber that is pierced with openings and a fluid circulation space in the vicinity of said openings of the chamber, and whereby said chamber is connected to a transfer line that extends between the chamber and a point that is located outside of the column; during a period T of the cycle, an injection and a draw-off of each materials into and from a distribution chamber that belongs to different plates are carried out, with the process being characterized in that, at an appropriate flow rate, a fluid volume is permanently circulated that circulates in the column in a bypass line that connects different chambers of the distributor plates; the flushing liquid has a composition close to the circulating fluid. The object thereof lies in avoiding greater composition difference between the flushing materials introduced from outside and the materials in the adsorption column to cause disturbance to the separation process. However, such solution will also cause a problem, i.e. a stream of the feedstocks not passing through the adsorption chamber, which is equivalent to a stream of channeling in the adsorption bed, and is adverse to the adsorption separation.

U.S. Pat. No. 6,004,518 discloses a high-purity simulated moving bed adsorptive separation apparatus, comprising a series of individual adsorbent chambers adapted for retaining a bed of adsorbent, a series of fluid transfer lines interconnecting the adsorbent chambers and also allowing passage of feedstock and desorbent streams into the apparatus and removal of extract and raffinate streams from the apparatus, a series of valves for controlling the flow of fluids through the fluid transfer lines and between adsorbent chambers, with a separate set of valves being associated with each adsorbent chamber and with said valves being characterized in that two ports of each valve which controls the flow of the feed stream into a specific adsorbent chamber are connected to the fluid transfer line which connects this specific adsorbent chamber with a next upstream adsorbent chamber; whereby fluid discharged from the next upstream adsorbent chamber may flow through the valve and flush the feed stream from the valve and from a conduit leading from this valve to the specific adsorbent chamber. However, each bed of adsorbent is required to be separate, and the circulating fluid entering the next bed from the previous bed needs to pass through the lines and valve.

SUMMARY OF THE INVENTION

The object of the present invention is to provide a process and device for separating a high purity product from the isomer mixtures by SMB adsorption, which has a higher yield or a higher treating capacity while ensuring the purity of the target product to be separated by adsorption.

The process for separating isomers by simulated moving bed (SMB) adsorption of present invention comprises separating the feedstock comprising isomers by SMB adsorption, said SMB comprising many beds of adsorbent each of which is equipped with grids, each of the grids being equipped with the feedstock inlet and outlet pipeline of the bed, the materials charged into and discharged from SMB at least comprising feedstock, desorbent, extract, and raffinate, the extract being enriched with the target product, characterized in that the extract is used as a flushing liquid and respectively charged to first or second bed at the upstream of the feedstock charging position and to one of second to fourth beds at the downstream of the extract withdrawing position.

The process of the present invention controls the inlet and outlet materials of SMB by means of multi-values, uses the extract as the flushing liquid for two flushings both of which are conducted in the purification zone. One flushing liquid is charged to first or second bed at the upstream of the feedstock charging position and another flushing liquid is charged to one of second to fourth beds at the downstream of the extract withdrawing position. Before the extract is withdrawn, the pipeline of the bed is flushed so as to ensure the purity of the target product separated by adsorption and has a higher yield or a higher treating capacity as compared with the prior art.

DETAILED DESCRIPTION OF THE INVENTION

The present invention discloses the extract as the flushing liquid for the pipeline of bed, and charging to different beds in two streams. Since the composition of the flushing liquid charged to the bed is similar to that of the bed which the flushing liquid is charged, the effect of the charged flushing liquid on the bed is decreased to the minimum, so as to effectively increase the adsorption efficiency.

The simulated moving adsorption bed used for separation by adsorption according to the present process comprises one or more adsorption columns, each of which is separated with grids to many beds of adsorbent, wherein said grids have the following functions: re-distributing the materials from the previous bed to the next bed, homogeneously mixing the materials introduced from outside with the materials from the previous bed, and withdrawing a part of the materials from the previous bed from the adsorption column. The grids permit the passage of the liquid and intercept the adsorbent particles from escaping from the bed of adsorbent, wherein the upper and lower surfaces thereof are generally the woven wire cloth, metal sintering screen or Johnson Screen. The materials introduced from outside to a certain bed, and the materials withdrawn from previous bed and out of the adsorption column are charged and discharged from the bed via a pipeline connected with the bed grids.

The materials charged to and discharged from the adsorption column at least comprise the feedstock (F), desorbent (D), extract (E) and raffinate (R). The feedstocks are the mixtures comprising at least two or more components which include the target product purified by adsorption separation; the components in the feedstocks have different adsorptive selectivities on the adsorbents, and the adsorbents have higher adsorptive selectivities to the target products. The desorbent should be greatly different from the feedstocks in the boiling point, and may be separated from the components in the feedstocks by rectification. The extract is enriched with the target product, and comprises a part of the desorbent at the same. The raffinate comprises a small amount of the target product; the less the content thereof is, the higher the adsorption separation efficiency is; the main components in the raffinate are the desorbent and other components in the feedstocks than the target product. The desorbent is recycled from the extract and raffinate by the rectification column.

According to the flow direction of the materials, the adsorption column is divided into the desorption zone, purification zone, adsorption zone and isolation zone. The bed of adsorbent between the desorbent charging and the extract withdrawal is the desorption zone; the bed of adsorbent between the extract withdrawal and the feedstock charging is the purification zone; the bed of adsorbent between the feedstock charging and the raffinate withdrawal is the adsorption zone; the bed of adsorbent between the raffinate withdrawal and the desorbent charging is the isolation zone. The simulated moving bed has from 6 to 30 beds, preferably from 12 to 24 beds. Two adsorption columns are generally used, totaling 24 beds, wherein 4-6 beds are the desorption zone; 8-10 beds are the purification zone; 6-8 beds are the adsorption zone; 2-3 beds are the isolation zone. In the present invention, the upstream and downstream of the charging and discharging positions of some certain materials at which the flushing liquid is charged are relative to the bed of the charging and discharging positions of said materials in the adsorption column. If along with the flow direction of the materials in the adsorption column, it is the downstream, and the opposite is the upstream. For example, the flushing liquid is charged to one bed at the downstream of the extract withdrawal position, i.e. the flushing liquid is charged to the next bed of the extract withdrawal position along with the flow direction of the materials of the bed.

In order to minimize the volume of the residual materials need to be flushed, the present invention discloses connecting each charging and discharging materials to the pipelines linked to the grids and controls said materials with respective on-off valves, which enables the on-off valves to get close to the adsorption column to the greatest extent and thereby reduces the volume of the pipelines.

If there are n streams of charging and discharging materials, and m beds in the adsorption column, there are n×m on-off valves altogether. At some certain moment, on-off valves connecting each stream of charging and discharging materials with different beds are in an open state, and the remaining is in a close state. At a specific time interval, i.e. a step time, the positions of the charging and discharging materials all move down a bed. The charging and discharging materials along with the flow direction of the materials in the adsorption column are in a sequence of the desorbent (D), extract (D), feedstock (F) and raffinate (R), and the circulation of materials in the adsorption column makes up a closed-loop. As for each bed, the charging and discharging materials are in a sequence of the raffinate (R), feedstock (F), extract (E) and desorbent (D) in cycles. The charging and discharging intervals of the materials are different, depending on the number of the adsorption bed separated between the adjacent materials, i.e. the number of the step time between two adjacent charging and discharging materials in the same bed is equal to the number of the beds between two adjacent charging and discharging materials corresponding to the adsorption column. For example, the bed between the desorbent charging and the extract withdrawal is the desorption zone having 5 beds; as for a certain bed, the extract is withdrawn from such bed 5 step time before the charging of the desorbent.

In order to eliminate the effect of the residual materials in the delivery materials pipelines on the adsorption separation process, and to ensure the separation of high purity target product, the pipelines through which the feedstocks pass and through which the extract will pass need to be flushed. However, the adverse effect of the flushing on the adsorption separation process shall be avoided while high purity products are produced. The present invention discloses flushing the pipelines by charging the extract at two different positions of the purification zone to make the composition of the residual materials in the bed pipelines after flushing close to the composition of the materials which will pass the pipelines, and to make the composition of the materials charged to the bed close to the composition of the materials in the bed, so as to minimize the effect of flushing on the adsorption separation.

One of two positions at which the flushing liquids are charged is close to the feedstock charging point and at first or second bed at the upstream of the feedstock charging bed; the other is close to the extract withdrawing point and at one of second to fourth beds at the downstream of the extract withdrawing position for flushing the residual materials and avoid the pollution of the extract to be withdrawn.

In a step time, the volume charging amount of the flushing liquid charged to first or second bed at the upstream of the feedstock charging bed is from 1.0 to 2.5, preferably from 1.2 to 2.0 times of the total volume of the pipelines from the flushing liquid control valves to the bed grids. The residual materials in the pipelines are flushed in such a flushing amount. The materials charged to the adsorption column are the mixture of the feedstocks and extract, and the average composition thereof is close to the composition of the liquid phase materials at the bed position at which the flushing fluid is charged in the adsorption column.

In a step time, the volume charging amount of the flushing liquid charged to one of second to fourth beds at the downstream of the extract withdrawing position is from 0.5 to 1.5, preferably from 0.6 to 1.0 times of the total volume of the pipelines from the flushing liquid control valves to the bed grids. The pipelines are flushed at the position at which the flushing fluid is charged, and the materials charged to the adsorption column are the extract slightly polluted by the residual feedstocks. The composition of the flushing fluid obtained by flushing according to said flushing amount is close to the composition of the liquid phase materials at the selected positions in the adsorption column into which the flushing liquid is charged.

Except for charging the extract as the flushing liquid of the pipeline at different positions of the purification zone, the present invention further discloses preferably charging the desorbent to first or second bed at the upstream of the extract withdrawing line for flushing the bed.

The separation process by adsorption of the present invention is the liquid phase separation process, wherein the operating temperature ranges from 20 to 330° C., preferably from 100 to 180° C.; the operating pressure enabling the system to be full liquid phase is preferably from 0.8 to 1.2 MPa, and from 0.6 to 1.0 MPa when p-xylene is separation by adsorption.

The isomers to be separated by adsorption according to the process of the present invention are preferably xylene and ethyl benzene, and the target product to be separated by adsorption is preferably p-xylene or m-xylene.

The present invention provide a device for separating isomers by simulated moving bed (SMB) adsorption, comprising SMB and the materials inlet and outlet pipelines, said SMB comprising many beds of adsorbent each of which is equipped with grids, each of the grids being equipped with the materials inlet and outlet pipeline of the bed, two flushing liquid pipelines being set up in parallel on the materials inlet and outlet pipeline between the beds, each of the flushing liquid pipelines being equipped with an on-off valve, the extract being used as the flushing liquid, the flushing liquid in one flushing liquid pipeline being charged to first or second bed at the upstream of the feedstock charging bed, and the flushing liquid in the other flushing liquid pipeline being charged to one of second to fourth beds at the downstream of the extract withdrawing position.

Preferably, a materials inlet and outlet pipeline is set up on the grids of each bed, and many on-off valves connected in parallel are set up on the pipeline to control the charging and discharging of each materials of the bed. The amount of the on-off valves set up on the materials inlet and outlet pipeline of each bed ranges from 6 to 7, i.e. there are 6 to 7 materials charged into or discharged from each bed. Preferably, three flushing pipelines are set up, wherein two of them use the extract as the flushing fluid, and the third one uses the desorbent as the flushing fluid, and the charging position is one bed at the upstream of the extract withdrawing position.

The present invention is further illustrated by the description of the drawings.

Figure 1:
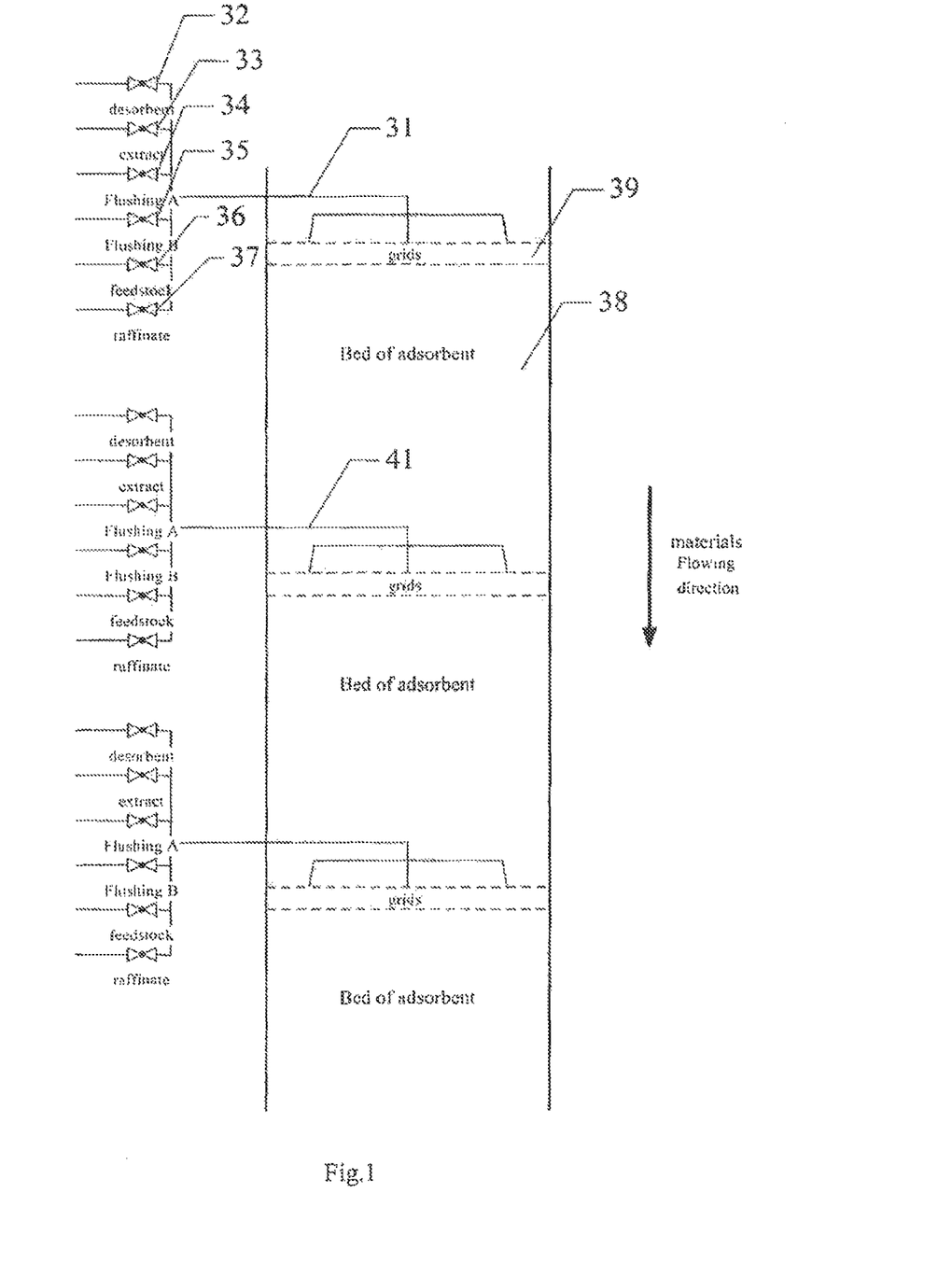
FIG. 1 shows the diagrammatic representation the structure of the adsorption bed in SMB in the present invention.

FIG. 1 shows the diagrammatic representation of the individual bed of adsorbent in SMB according to the process of the present invention. Grids 39 are located above the bed 38; two flushings, i.e. flushing A and flushing B, are set up for each bed. There are six streams of charging and discharging materials; each materials pipeline is connected with grids 39 via a materials charging and discharging pipeline 31; six streams of charging and discharging materials are connected with the materials charging and discharging pipeline 31 via six separate pipelines each of which is equipped with a feedstock charging and discharging control valve. Specifically, the desorbent control valve 32 controls the charging of the desorbent; the extract control valve 33 controls the withdrawal of the extract; the flushing liquid A control valve 34 controls the charging of the flushing liquid A, wherein the charging position is close to the withdrawing position of the extract, and the flushing liquid is the extract;

the flushing liquid B control valve 35 controls the charging of the flushing liquid B, wherein the charging position is close to the feedstock charging position; the feedstock control valve 36 controls the charging of the feedstocks; the raffinate control valve 37 controls the withdrawal of the raffinate.

Figure 2:
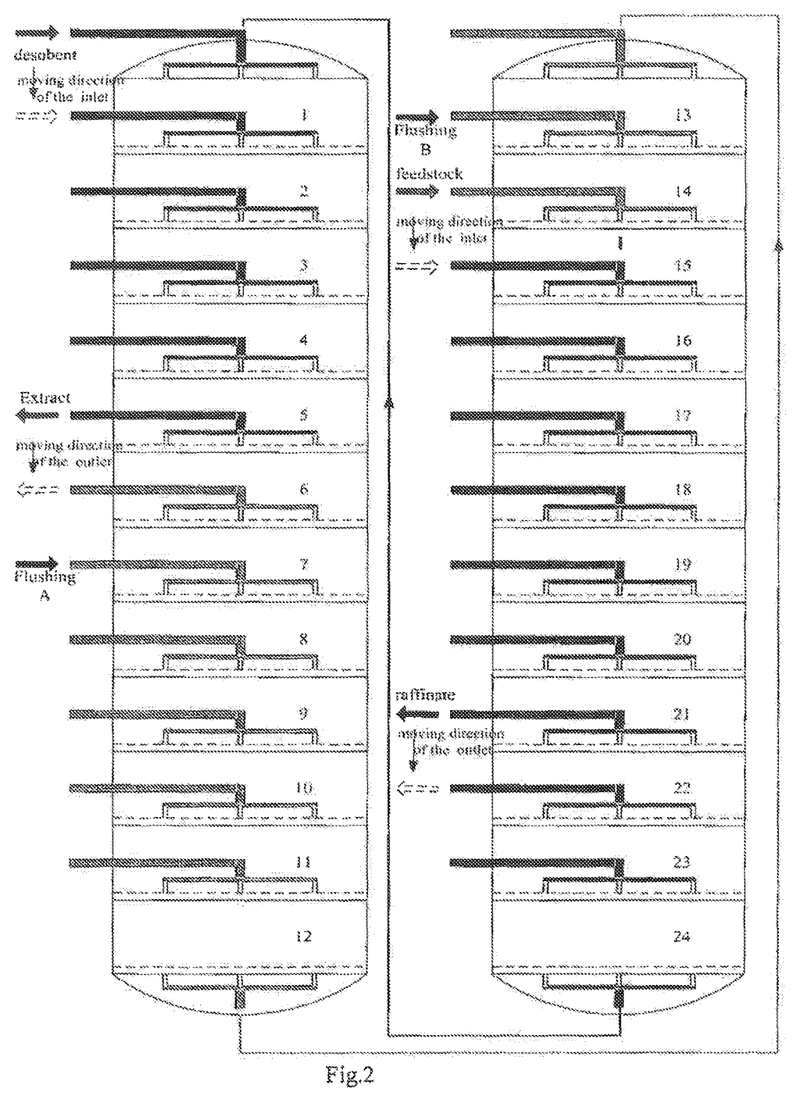
FIG. 2 shows the diagrammatic representation of the position at which the flushing liquid is charged in the present invention process.

According to FIG. 2, it can be seen that the simulated moving adsorption bed has 24 beds isolated by grids. According to FIG. 1, each of the bed is equipped with 6 materials charging and discharging pipelines, and there are 6×24 on-off valves altogether for 24 beds. The desorption zone between the desorbent charging and the extract withdrawal has 5 beds; the purification zone between the extract withdrawal and the feedstock charging has 9 beds; the adsorption zone between the feedstock charging and the raffinate withdrawal has 7 beds; and the isolation zone between the raffinate withdrawal and the desorbent charging has 3 beds. At some certain moment, 6 on-off valves connecting each stream of charging and discharging materials with different beds are in an open state, and the others are in a close state. At a specific time interval, i.e. a step time, the position of each of the charging and discharging materials all moves down a bed. A step time ranges from 45 to 200 seconds. The circulation of materials in the adsorption column makes up a closed-loop, and the circulating pump provides the materials circulation with power. The flow rate of the circulating pump is controlled according to the flow rate as required in the zone in which it is located, and the number thereof is equal or less than that of the adsorption columns. A flushing pump may be set up between the total extract pipeline and the total flushing liquid pipeline, wherein the extract is recycled to the system as the flushing liquid. A flushing pump may also be set up after the extract buffer tank, wherein the extract is recycled to the system as the flushing liquid. A flowmeter and a flow control valve are set up for two flushings respectively to control the flow rate of the flushing liquids A and B.

According to FIG. 1, the charging and discharging materials in a certain bed is controlled by the following method: on the assumption that, at a certain moment, the desorbent begins to enter the bed via the pipeline 31 connected with the grids above the bed, wherein such bed is located in the desorption zone; after a step time t, the charging of the desorbent to the pipeline 31 connected with the grids above the bed stops, and the desorbent is charged to the next bed by charging to the pipeline 41 connected with the grids above the next bed. No materials is charged to or discharged from the original bed located in the isolation zone. Since there are 3 beds, three step times are required. At the 4×t moment, the raffinate is discharged from the bed via the pipeline 41 connected with the grids below the bed which enters the adsorption zone. After 6 step times and at the 10×t moment, the feedstocks begin to enter the bed via the pipeline 31 connected with the grids above the bed which is still located in the adsorption zone. At the 11×t moment, the flushing liquid B enters the bed, and the bed enters the purification zone at this time. After 6 step times and at the 17×t moment, the flushing liquid A charged to two beds below the extract begins to be charged to the pipeline 31 connected with the grids above the bed and enters the bed, wherein such bed is still located in the purification zone at this time. After 3 step times and at the 20×t moment, the extract begins to be discharged from the bed via the pipeline 41 connected with the grids below the bed, wherein the bed is located in the desorption zone at this time. After another 4 step times and at the 24×t moment, the desorbent re-enters the bed via the pipeline 31 connected with the grids above the bed, so as to complete a full cycle.

Figure 3:
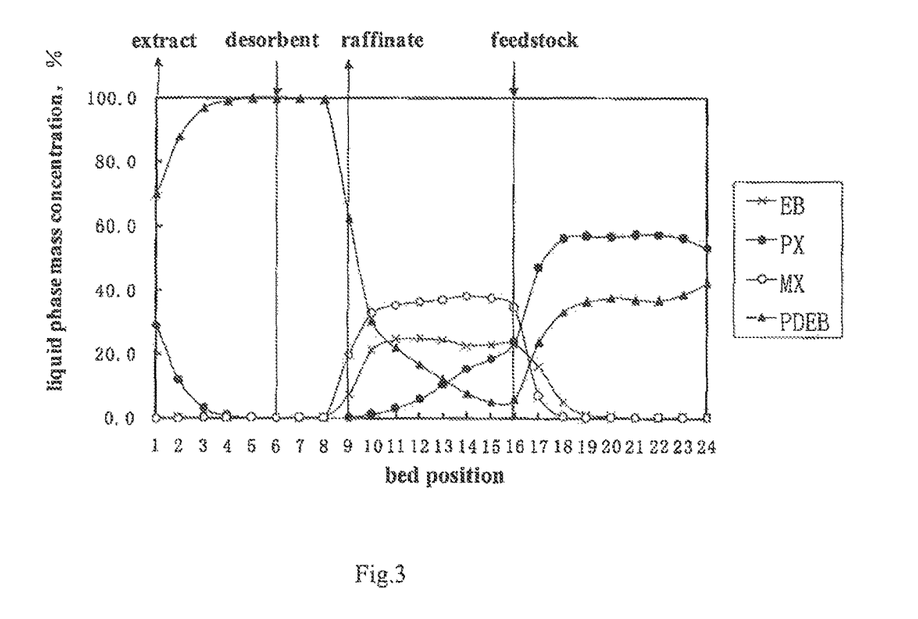
FIG. 3 shows the concentration distributing graph of the liquid phase materials in the adsorption column while the mixed xylene is separated by adsorption.

FIG. 3 shows the distribution graph of the liquid phase feedstocks in a SMB having 24 beds, involving the process of separating PX from the $C_8$ aromatic isomer mixtures comprising ethylbenzene (EB), p-xylene (PX), m-xylene (MX) and o-xylene (OX), wherein the desorbent is p-diethyl benzene (PDEB).

While the present invention is used to separate p-xylene (PX) from the mixtures of $C_8$ aromatic isomers, the product purity is required to be at least 99.5 mass %, more preferably greater than 99.7 mass %, The desorbent is preferably p-diethyl benzene (PDEB), and the adsorbent is preferably faujasite exchanged with barium or/and potassium. Two adsorption columns are generally used, totaling 24 beds, wherein 4-6 beds are the desorption zone; 8-10 beds are the purification zone; 6-8 beds are the adsorption zone; 2-3 beds are the isolation zone, While the present invention is used to separate m-xylene (MX) from the mixtures of $C_8$ aromatic isomers, the product purity is required to be at least 99.5 mass %, more preferably greater than 99.7 mass %, The desorbent is preferably toluene, and the adsorbent is preferably faujasite exchanged with alkali metal ions.

The present process can also be used for separation of p-xylene from other $C_8$ aromatic isomers, m-xylene from other $C_8$ aromatic isomers, ethylbenzene from other $C_8$ aromatic isomers, n-alkanes from hydrocarbons having other structures, n-alkanes and monomethyl branched paraffin from hydrocarbons having other structures, alkenes from alkanes.

The present invention is further illustrated by, but is not limited to the following examples,

EXAMPLE 1

The process of the present invention was used to separate p-xylene. P-xylene was separated by SMB adsorption, wherein SMB had 24 beds; the desorption zone had 5 beds; the purification zone had 9 beds; the adsorption zone had 7 beds; the isolation zone had 3 beds; the step time was 80 seconds; the operating temperature was 177° C.; the operating pressure was 0.88 MPa. The adsorbent was RAX-2000A-type adsorbent produced by SIPOPEC catalyst company, with the main component being X-type molecular sieves exchanged with barium ions. An individual on-off value was set up for each stream of the inlet and outlet feedstocks into/from each bed. A first flushing $C_1$ which was desorbent was set up and charged to first bed at the upstream of the extract withdrawing point; a second flushing A was the extract and charged to second bed at the downstream of the extract withdrawing point; a third flushing B was the extract and charged to first bed at the upstream of the feedstock charging point. As for a certain bed, the volume of the pipelines through which the flushing liquid passed was 0.75% of the volume of a single bed; the desorbent was p-diethyl benzene.

As for each bed, the bed was flushed first with a flushing B and then with a flushing A along with the flow direction of the materials, wherein the extract volumes used for the flushing A and B were different. The feedstock for adsorption separation, the composition of the materials in the bed that flushing A and B charged to, and the composition of the materials charged to the bed while the flushing liquids in different amounts are used for flushing are listed in Table 1.

According to the data in Table 1, it can be seen that, when the volume of the flushing B was 1.2 and 1.7 times of the pipelines passed (referring to the total volume of the pipelines of an individual bed), the composition of the materials charged to the bed was slightly different from those of the materials in first and second bed at the upstream of the feedstock charging point, and greatly different from materials of third bed at the upstream of the feedstock charging point. Thus the flushing B was suitably charged to first or second bed at the upstream of the feedstock charging point, and not suitably charged to third bed at the upstream of the feedstock charging point.

In addition, it can be seen according to the data at last two lines of Table 1 that the composition of the materials flushing A charged to the bed was slightly different from those of the materials in second to fourth bed at the downstream of the extract withdrawing point, and greatly different from that of the materials in first or fifth bed at the downstream of the extract withdrawing point. Thus the flushing A was suitably charged to second to fourth beds at the downstream of the extract withdrawing point, and not suitably charged to first or fifth bed at the downstream of the extract withdrawing point.

EXAMPLE 2

P-xylene was separated from the mixed xylenes by SMB adsorption, wherein SMB had 24 beds; the desorption zone had 5 beds; the purification zone had 9 beds; the adsorption zone had 7 beds; the isolation zone had 3 beds; the step time was 85 seconds; the operating temperature was 177° C.; the operating pressure was 0.88 MPa. The composition of the mixed xylene feedstocks is listed in Table 1. The adsorbent was the same as Example 1.

An individual on-off valve was set up for each stream of the inlet and outlet materials into/from each bed. A first flushing $C_1$ which was composed of the desorbent was set up and charged to first bed at the upstream of the extract withdrawing point; a flushing A was the extract and charged to third bed at the downstream of the extract withdrawing point; a flushing B was the extract and charged to first bed at the upstream of the feedstock charging point. As for a certain bed, the volume of the pipelines through which the flushing liquid passed was 0.75% of the volume of a single bed; the desorbent was p-diethyl benzene.

As for each bed, the amount of the flushing liquid used for each flushing was represented with the percent of the volume of the pipelines through which the flushing liquid passed (the same below). Under the circumstance of ensuring that the purity of p-xylene is about 99.7 mass %, the p-xylene yield and the amount of the flushing liquids in a step time are listed in Table 2.

EXAMPLE 3

According to the process in Example 2, p-xylene was separated from the mixed xylenes by SMB adsorption, with the difference in the amount of the flushing liquid used for each flushing. Under the circumstance of ensuring that the purity of p-xylene is about 99.7 mass %, the p-xylene yield and the amount of the flushing liquids in a step time are listed in Table 2.

EXAMPLE 4

According to the process in Example 2, p-xylene was separated from the mixed xylenes by SMB adsorption, with the difference in the amount of the flushing liquid used for each flushing. As for a certain bed, the volume of the pipelines through which the flushing liquid passed was 1.5% of the volume of a single bed. Under the circumstance of ensuring that the purity of p-xylene is about 99.7 mass %, the p-xylene yield and the amount of the flushing liquids in a step time are listed in Table 2.

COMPARATIVE EXAMPLES 1-3

The operation was conducted according to the process for separating PX from the mixed xylenes by SMB adsorption in the current industry. SMB had 24 adsorption beds; the desorption zone had 5 beds; the purification zone had 9 beds; the adsorption zone had 7 beds; the isolation zone had 3 beds; the step time was 85 seconds; the operating temperature was 177° C.; and the operating pressure was 0.88 MPa. A rotary valve was used to connect each pipeline of the bed to all beds; a flushing liquid withdrawing outlet (Hout) was set up, withdrawn at first bed at the downstream of the desorbent charging point, pumped to the flushing liquid inlet (Hin), i.e. the second bed at the upstream of the feedstock charging point; A flushing X which was composed of the desorbent was set up and charged to first bed at the downstream of the extract withdrawing point. A flushing Hin and a flushing Hout were calculated as two flushing of the materials. As for a certain bed, the volume of the pipelines through which the flushing liquid passed was 1.5% of the volume of a single bed. The feedstocks were those as shown in Table 1, and the desorbent and adsorbent were the same as those in Example 2. Under the circumstance of ensuring that the purity of p-xylene is about 99.7 mass %, the p-xylene yield and the amount of the flushing liquids in a step time are listed in Table 2. The p-xylene yield was notably lower than that in the examples of the present invention, With other conditions being the same as those in Comparative Example 1, a higher p-xylene yield could also be achieved by reducing the flow rate of adsorption feedstocks by 8%, and the results were also listed in Table 2.

TABLE 1

| name of materials | Composition, mass % | | | | | PX concentration normalized according to C8Aromatics, mass % |
| --- | --- | --- | --- | --- | --- | --- |
| | EB | PX | MX | OX | PDEB | |
| Extract | 0.05 | 30.0 | 0.03 | 0.01 | 69.91 | 99.70 |
| Feedstocks | 23.5 | 22.06 | 45.3 | 9.14 | 0 | 22.06 |
| first Bed at the upstream of the feedstock charging point | 24.76 | 25.35 | 38.61 | 5.41 | 5.88 | 26.93 |
| second Bed at the upstream of the feedstock charging point | 16.29 | 47.11 | 7.03 | 1.15 | 28.42 | 65.81 |

TABLE 1-continued

| name of materials | Composition, mass % | | | | | PX concentration normalized according to C8Aromatics, mass % |
|---|---|---|---|---|---|---|
| | EB | PX | MX | OX | PDEB | |
| third Bed at the upstream of the feedstock charging point | 4.83 | 56.04 | 0.59 | 0.19 | 38.35 | 90.90 |
| materials charged to the bed when the volume of flushing B is 1.2 times of the pipelines passed | 19.59 | 23.38 | 37.76 | 7.62 | 11.65 | 26.47 |
| materials charged to the bed when the volume of flushing B is 1.7 times of the pipelines passed | 13.84 | 25.33 | 26.66 | 5.38 | 28.79 | 35.57 |
| first Bed at the downstream of the extract withdrawing point | 0.11 | 53.15 | 0.06 | 0.02 | 46.66 | 99.65 |
| second Bed at the downstream of the extract withdrawing point | 0.18 | 56.14 | 0.07 | 0.03 | 43.59 | 99.50 |
| third Bed at the downstream of the extract withdrawing point | 0.27 | 57.42 | 0.09 | 0.04 | 42.18 | 99.31 |
| fourth Bed at the downstream of the extract withdrawing point | 0.36 | 57.24 | 0.11 | 0.05 | 42.24 | 99.10 |
| fifth Bed at the downstream of the extract withdrawing point | 0.59 | 56.53 | 0.14 | 0.05 | 42.69 | 98.64 |
| materials charged to the bed when the volume of flushing A is 1.0 times of the pipelines passed (the pipeline had been flushed by volume of flushing B with 1.2 times volume of the pipelines passed) | 0.12 | 29.98 | 0.17 | 0.04 | 69.70 | 98.93 |
| materials charged to the bed when the volume of flushing A is 0.7 times of the pipelines passed (the pipeline had been flushed by volume of flushing B with 1.7 times volume of the pipelines passed) | 0.10 | 29.98 | 0.12 | 0.03 | 69.77 | 99.19 |

TABLE 2

| | Flushing method | | | Results of the adsorption separation | |
|---|---|---|---|---|---|
| Example No. | $C_1$ or Hout amount | A or X amount | B or Hin amount | PX purity, mass % | PX yield, mass % |
| 2 | 100% | 70% | 130% | 99.73 | 98.2 |
| 3 | 100% | 90% | 110% | 99.70 | 97.9 |
| 4 | 100% | 70% | 130% | 99.72 | 95.8 |
| Com. Exp. 1 | 130% | 70% | 130% | 99.72 | 91.4 |
| Com. Exp. 2 | 110% | 90% | 110% | 99.70 | 88.2 |
| Com. Exp. 3 (the feedstock flow rate is reduced by 8%) | 130% | 70% | 130% | 99.71 | 98.0 |

According to the data in Table 2, it can be seen that, under the circumstance of ensuring the substantially same xylene purity, the present process has a higher p-xylene yield or a higher treating capacity than the comparative examples.

The invention claimed is:

1. A process for separating isomers by simulated moving bed (SMB) adsorption comprising separating a feedstock comprising isomers by SMB adsorption, said SMB comprising many adsorption beds each of which is equipped with grids, each of the grids being equipped with a materials charging and discharging pipeline of each adsorption bed, the materials charged into and discharged from SMB at least comprising feedstock, desorbent, extract and raffinate, the extract being enriched with a target product, characterized in that the extract is used as a flushing liquid and respectively charged to first bed upstream of a feedstock charging position and to one of second to fourth beds downstream of an extract withdrawing position,
    wherein, in a step time, the volume charging amount of the flushing liquid charged to first bed upstream of the feedstock charging position is from 1.0 to 2.5 times of the total volume of the pipelines from flushing liquid control valves to the grids of the bed of adsorbent, and the volume charging amount of the flushing liquid charged to one of second to fourth beds downstream of the extract withdrawing position is from 0.5 to 1.5 times of the total volume of the pipelines from the flushing liquid control valves to the grids of the bed of the adsorbent.

2. The process according to claim 1, characterized in that a desorbent is charged to first or second bed upstream of an extract withdrawing position to wash pipeline of the bed.

3. The process according to claim 1, characterized in that the separation process by adsorption is a liquid phase separation process.

4. The process according to claim 1, characterized in that, in a step time, the charging and discharging materials along with a flow direction of the materials in SMB are in a sequence of the desorbent, the extract, the feedstock, and the raffinate.

5. The process according to claim 1, characterized in that said SMB comprises many beds, which are divided into a desorption zone, a purification zone, an adsorption zone, and an isolation zone.

6. The process according to claim 1, characterized in that the isomers separated by adsorption are xylenes and ethylbenzene, and the target product to be separated by adsorption is p-xylene or m-xylene.

7. The process according to claim 1, characterized in that the desorbent for separation by adsorption is p-diethyl benzene or toluene.

* * * * *